United States Patent
Arepally et al.

(10) Patent No.: US 9,889,031 B1
(45) Date of Patent: Feb. 13, 2018

(54) METHOD OF GASTRIC ARTERY EMBOLIZATION

(71) Applicant: Surefire Medical, Inc., Westminster, CO (US)

(72) Inventors: Aravind Arepally, Atlanta, GA (US); James E. Chomas, Denver, CO (US)

(73) Assignee: Surefire Medical, Inc., Westminster, CO (US)

( * ) Notice: Subject to any disclaimer, the term of this patent is extended or adjusted under 35 U.S.C. 154(b) by 866 days.

(21) Appl. No.: 14/259,489

(22) Filed: Apr. 23, 2014

Related U.S. Application Data

(63) Continuation-in-part of application No. 14/259,293, filed on Apr. 23, 2014, now Pat. No. 9,770,319.

(60) Provisional application No. 61/970,202, filed on Mar. 25, 2014.

(51) Int. Cl.
  A61F 5/00  (2006.01)
  A61M 5/48  (2006.01)

(52) U.S. Cl.
  CPC ........... *A61F 5/0076* (2013.01); *A61M 5/488* (2013.01)

(58) Field of Classification Search
  CPC ... A61F 5/0076; A61M 5/488; A61M 25/003; A61M 2025/0039; A61M 5/142; A61M 5/48
  See application file for complete search history.

(56) References Cited

U.S. PATENT DOCUMENTS

| | | |
|---|---|---|
| 4,738,740 A | 4/1988 | Pinchuk et al. |
| 5,234,425 A | 8/1993 | Fogarty et al. |
| 5,893,869 A | 4/1999 | Barnhart et al. |
| 5,895,399 A | 4/1999 | Barbut et al. |
| 5,910,154 A | 6/1999 | Tsugita et al. |
| 5,911,734 A | 6/1999 | Tsugita et al. |
| 6,001,118 A | 12/1999 | Daniel et al. |
| 6,010,522 A | 1/2000 | Barbut et al. |
| 6,027,520 A | 2/2000 | Tsugita et al. |
| 6,042,598 A | 3/2000 | Tsugita et al. |
| 6,059,745 A | 5/2000 | Gelbfish |
| 6,152,946 A | 11/2000 | Broome et al. |
| 6,165,200 A | 12/2000 | Tsugita et al. |
| 6,168,579 B1 | 1/2001 | Tsugita |

(Continued)

FOREIGN PATENT DOCUMENTS

| | | |
|---|---|---|
| EP | 1226795 | 7/2002 |
| EP | 1803423 | 7/2007 |

(Continued)

OTHER PUBLICATIONS

US 7,169,126, 01/2007, Zadno-Azizi (withdrawn)

(Continued)

*Primary Examiner* — Nathan R Price
*Assistant Examiner* — Melissa A Snyder
(74) *Attorney, Agent, or Firm* — Gordon & Jacobson, P.C.

(57) ABSTRACT

A method of bariatric embolization includes deploying an intravascular pressure modulating device at a target location, operating the pressure modulating device to reduce pressure within the fundus, and infusing an embolizing agent into the fundus. Use of the pressure modulating device prevents delivery of the embolizing agent into proximal and distal non-target vessels. The method takes advantage of unique flow and pressure dynamics of the arterial vessels in the stomach.

13 Claims, 5 Drawing Sheets

(56) References Cited

U.S. PATENT DOCUMENTS

| | | |
|---|---|---|
| 6,179,851 B1 | 1/2001 | Barbut et al. |
| 6,235,044 B1 | 5/2001 | Root et al. |
| 6,258,120 B1 | 7/2001 | McKenzie et al. |
| 6,306,074 B1 | 10/2001 | Waksman et al. |
| 6,306,163 B1 | 10/2001 | Fitz |
| 6,309,399 B1 | 10/2001 | Barbut et al. |
| 6,361,545 B1 | 3/2002 | Macoviak et al. |
| 6,371,969 B1 | 4/2002 | Tsugita et al. |
| 6,371,971 B1 | 4/2002 | Tsugita et al. |
| 6,383,206 B1 | 5/2002 | Gillick et al. |
| 6,395,014 B1 | 5/2002 | Macoviak et al. |
| 6,436,112 B2 | 8/2002 | Wensel et al. |
| 6,443,926 B1 | 9/2002 | Kletschka |
| 6,485,456 B1 | 11/2002 | Kletschka |
| 6,485,502 B2 | 11/2002 | Don Michael et al. |
| 6,499,487 B1 | 12/2002 | McKenzie et al. |
| 6,530,935 B2 | 3/2003 | Wensel et al. |
| 6,533,800 B1 | 3/2003 | Barbut |
| 6,537,294 B1 | 3/2003 | Boyle et al. |
| 6,537,297 B2 | 3/2003 | Tsugita et al. |
| 6,540,722 B1 | 4/2003 | Boyle et al. |
| 6,551,303 B1 | 4/2003 | Van Tassel et al. |
| 6,582,396 B1 | 6/2003 | Parodi |
| 6,589,264 B1 | 7/2003 | Barbut et al. |
| 6,592,546 B1 | 7/2003 | Barbut et al. |
| 6,607,506 B2 | 8/2003 | Kletschka |
| 6,620,148 B1 | 9/2003 | Tsugita |
| 6,635,070 B2 | 10/2003 | Leeflang et al. |
| 6,645,220 B1 | 11/2003 | Huter et al. |
| 6,645,222 B1 | 11/2003 | Parodi et al. |
| 6,645,223 B2 | 11/2003 | Boyle et al. |
| 6,652,555 B1 | 11/2003 | VanTassel et al. |
| 6,652,556 B1 | 11/2003 | VanTassel et al. |
| 6,656,351 B2 | 12/2003 | Boyle |
| 6,673,090 B2 | 1/2004 | Root et al. |
| 6,676,682 B1 | 1/2004 | Tsugita et al. |
| 6,689,150 B1 | 2/2004 | VanTassel et al. |
| 6,692,508 B2 | 2/2004 | Wensel et al. |
| 6,692,509 B2 | 2/2004 | Wensel et al. |
| 6,692,513 B2 | 2/2004 | Streeter et al. |
| 6,695,813 B1 | 2/2004 | Boyle et al. |
| 6,695,858 B1 | 2/2004 | Dubrul et al. |
| 6,702,834 B1 | 3/2004 | Boylan et al. |
| 6,706,053 B1 | 3/2004 | Boylan et al. |
| 6,706,055 B2 | 3/2004 | Douk et al. |
| 6,730,108 B2 | 5/2004 | VanTassel et al. |
| 6,746,469 B2 | 6/2004 | Mouw |
| 6,818,006 B2 | 11/2004 | Douk et al. |
| 6,830,579 B2 | 12/2004 | Barbut |
| 6,837,898 B2 | 1/2005 | Boyle et al. |
| 6,855,154 B2 | 2/2005 | Abdel-Gawwad |
| 6,866,677 B2 | 3/2005 | Douk et al. |
| 6,887,258 B2 | 5/2005 | Denison et al. |
| 6,896,690 B1 | 5/2005 | Lambrecht et al. |
| 6,902,540 B2 | 6/2005 | Dorros et al. |
| 6,908,474 B2 | 6/2005 | Hogendijk et al. |
| 6,911,036 B2 | 6/2005 | Douk et al. |
| 6,936,060 B2 | 8/2005 | Hogendijk et al. |
| 6,939,362 B2 | 9/2005 | Boyle et al. |
| 6,964,670 B1 | 11/2005 | Shah et al. |
| 6,964,673 B2 | 11/2005 | Tsugita et al. |
| 6,974,469 B2 | 12/2005 | Broome et al. |
| 6,989,027 B2 | 1/2006 | Allen et al. |
| 7,044,958 B2 | 5/2006 | Douk et al. |
| 7,044,966 B2 | 5/2006 | Svanidze et al. |
| 7,066,946 B2 | 6/2006 | Douk et al. |
| 7,101,396 B2 | 9/2006 | Artof et al. |
| 7,162,303 B2 | 1/2007 | Levin et al. |
| 7,169,164 B2 | 1/2007 | Borillo et al. |
| 7,172,614 B2 | 2/2007 | Boyle et al. |
| 7,172,621 B2 | 2/2007 | Theron |
| 7,214,237 B2 | 5/2007 | Don Michael et al. |
| 7,217,255 B2 | 5/2007 | Boyle et al. |
| 7,223,253 B2 | 5/2007 | Hogendijk |
| 7,232,452 B2 | 6/2007 | Adams et al. |
| 7,232,453 B2 | 6/2007 | Shimon |
| 7,241,304 B2 | 7/2007 | Boyle et al. |
| 7,250,041 B2 | 7/2007 | Chiu et al. |
| 7,252,675 B2 | 8/2007 | Denison et al. |
| 7,279,000 B2 | 10/2007 | Cartier et al. |
| 7,306,575 B2 | 12/2007 | Barbut et al. |
| 7,322,957 B2 | 1/2008 | Kletschka et al. |
| 7,326,226 B2 | 2/2008 | Root et al. |
| 7,331,973 B2 | 2/2008 | Gesswein et al. |
| 7,338,510 B2 | 3/2008 | Boylan et al. |
| 7,344,549 B2 | 3/2008 | Boyle et al. |
| 7,371,249 B2 | 5/2008 | Douk et al. |
| 7,425,215 B2 | 9/2008 | Boyle et al. |
| 7,537,600 B2 | 5/2009 | Eskuri |
| 7,544,202 B2 | 6/2009 | Cartier et al. |
| 7,572,272 B2 | 8/2009 | Denison et al. |
| 7,582,100 B2 | 9/2009 | Johnson et al. |
| 7,585,309 B2 | 9/2009 | Larson |
| 7,591,832 B2 | 9/2009 | Eversull et al. |
| 7,604,650 B2 | 10/2009 | Bergheim |
| 7,647,115 B2 | 1/2010 | Levin et al. |
| 7,653,438 B2 | 1/2010 | Deem et al. |
| 7,833,242 B2 | 11/2010 | Gilson et al. |
| 7,842,084 B2 | 11/2010 | Bicer |
| 7,853,333 B2 | 12/2010 | Demarais |
| 7,873,417 B2 | 1/2011 | Demarais |
| 7,922,691 B2 * | 4/2011 | Kletschka ........ A61B 17/22032 |
| | | 604/96.01 |
| 7,937,143 B2 | 5/2011 | Demarais et al. |
| 8,257,384 B2 * | 9/2012 | Bates ..................... A61F 2/013 |
| | | 606/200 |
| 8,500,775 B2 | 8/2013 | Chomas et al. |
| 8,696,698 B2 | 4/2014 | Chomas et al. |
| 8,696,699 B2 | 4/2014 | Chomas et al. |
| 2002/0161390 A1 | 10/2002 | Mouw |
| 2002/0161394 A1 | 10/2002 | Macoviak et al. |
| 2003/0097114 A1 | 5/2003 | Ouriel et al. |
| 2003/0187474 A1 | 10/2003 | Keegan et al. |
| 2004/0068288 A1 | 4/2004 | Palmer et al. |
| 2004/0220609 A1 | 11/2004 | Douk et al. |
| 2004/0225354 A1 | 11/2004 | Allen et al. |
| 2004/0260333 A1 | 12/2004 | Dubrul et al. |
| 2005/0010285 A1 | 1/2005 | Lambrecht et al. |
| 2005/0015048 A1 | 1/2005 | Chiu et al. |
| 2005/0015112 A1 | 1/2005 | Cohn et al. |
| 2005/0119688 A1 | 6/2005 | Bergheim |
| 2005/0261759 A1 | 11/2005 | Lambrecht et al. |
| 2006/0167537 A1 | 7/2006 | Larsson et al. |
| 2006/0173490 A1 | 8/2006 | LaFontaine et al. |
| 2007/0106324 A1 | 5/2007 | Garner et al. |
| 2007/0179590 A1 | 8/2007 | Lu et al. |
| 2008/0033341 A1 | 2/2008 | Grad |
| 2008/0039786 A1 | 2/2008 | Epstein et al. |
| 2009/0018498 A1 | 1/2009 | Chiu et al. |
| 2009/0076409 A1 | 3/2009 | Wu et al. |
| 2009/0222035 A1 | 9/2009 | Schneiderman |
| 2011/0137399 A1 | 6/2011 | Chomas et al. |
| 2011/0288529 A1 | 11/2011 | Fulton |
| 2012/0116351 A1 | 5/2012 | Chomas et al. |
| 2012/0259206 A1 | 10/2012 | Roberts et al. |
| 2013/0079731 A1 | 3/2013 | Chomas et al. |
| 2013/0226166 A1 | 8/2013 | Chomas et al. |
| 2014/0207178 A1 | 7/2014 | Chomas et al. |

FOREIGN PATENT DOCUMENTS

| | | |
|---|---|---|
| WO | WO 99/16382 | 4/1999 |
| WO | WO 99/44510 | 9/1999 |
| WO | WO 01/41679 | 6/2001 |
| WO | WO 01/45592 | 6/2001 |
| WO | WO 01/49215 | 7/2001 |
| WO | WO 2004/043293 | 5/2004 |

OTHER PUBLICATIONS

A Study of the Geometrical and Mechanical Properties of a Self-Expandig Metallic Stent—Theory and Experiment, Dr. Michael R.

(56) References Cited

OTHER PUBLICATIONS

Jedwab, Claude O. Clerc, Journal of Applied Biomaterials, vol. 4, Issue 1, pp. 77-85, Spring 1993.
Finite Element Stent Design, M. De Beule, R. Van Impe, P. Verdonck, B. Verhegghe, Computer Methods in Biomechanics and Biomedical Engineering, 2005.
Catheter-Based Renal Sympathetic Denervation for Resistant Hypertension: a Multicentre Safety and Proof-of-Principle Cohort Study, Krum et al, The Lancet, 2009.
Renal Denervation as a Therapeutic Approach for Hypertension: Novel Implications for an Old Concept, Schlaich et al., Hypertension, Journal of the American Heart Association.
Renal Sympathetic-Nerve Ablation for Uncontrolled Hypertension, Schlaich et al, The New England Journal of Medicine, 2009, pp. 932-934.
Fusion Drug Delivery System-Novel Catheter/Stent Design for Targeted Drug Delivery, Gerschwind & Barnett, Non-Published US provisional patent application filed Sep. 17, 2.
Embolization II, Scientific Session 11, JVIR, Mar. 27, 2012.
Embolization procedure lowers levels of "hunger hormone," leads to weight loss, EurekAlert Public Release, Mar. 7, 2013.
First-In-Man Study of Left Gastric Artery Embolization for Weight Loss, Nicholas Kipshidze et al., ACC.13, E2056, JACC Mar. 12, 2013, vol. 61, Issue 10.
Left Gastric Embolization Leads to Weight Loss, Bariatriac News, Owen Haskins, Dec. 4, 2013.
U.S. Appl. No. 14/259,293, filed Apr. 23, 2014, Bryan Pinchuk et al.

\* cited by examiner

METHOD OF GASTRIC ARTERY EMBOLIZATION

CROSS-REFERENCE TO RELATED APPLICATIONS

This application is a continuation-in-part of U.S. Ser. No. 14/259,293, filed Apr. 23, 2014, which claims benefit of U.S. Provisional No. 61/970,202, filed Mar. 25, 2014, both of which are hereby incorporated by reference herein in their entireties.

BACKGROUND OF THE INVENTION

1. Field of Invention

The present invention relates generally to bariatric treatments. More particularly, this method relates to performing a gastric artery embolization procedure for the purpose of treating obesity.

2. State of the Art

Obesity is a chronic, metabolic state favoring a positive energy balance which results in excessive fat storage. It has highly significant associated medical, psychological, social, physical and economic co-morbidities. As presently understood, it is multifactorial, involving heredity, biochemical, hormonal, environmental, behavioral, public health and cultural elements. Morbid obesity, also referred to as severe obesity, typically is associated with a body mass index (BMI), i.e., the ratio of weight in kg to the square of the height in meters, of equal to, or in excess, of 40 kg/m$^2$.

Approximately 27 percent of Americans are obese. Mortality rates for morbidly obese individuals are more than twice as high as those for otherwise similar normal weight individuals. Co-morbidities associated with obesity include, for example, high blood pressure, hypertension, hypercholesterolemia, dyslipidemia, Type 2 (non-insulin dependent) diabetes, insulin resistance, glucose intolerance, hyperinsulinemia, and numerous other disease states. Over 7 percent of American have Type 2 diabetes, and almost 2 million Americans are newly diagnosed with Type 2 diabetes each year. With obesity as a major contributing factor to Type 2 diabetes and other disease states, morbid obesity is an extreme health hazard if left untreated.

Bariatric surgical procedures have been developed and are practiced as a means of controlling obesity and obesity related diseased states. Gastric bypass requires a significant surgical procedure for removing a portion of the gastrointestinal tract, and the gastrointestinal pathway is re-routed in a manner that promotes the sensation of satiety and prevents the absorption of calories in order to reduce patient weight. However, if the procedure is not accepted well by the patient, it is irreversible. Laparoscopic gastric banding is a reversible procedure that involves the placement of a band about the upper portion of the stomach to create a stoma which restricts the intake of food. Tubing connects the band to a subcutaneous port where injection of saline allows adjustment of pressure just below the gastro-oesophageal junction. Both of the procedures work, but they are expensive and require a relatively invasive surgical procedure.

Recently, investigational studies have determined that bariatric arterial embolization may be as efficacious as bariatric surgery. Referring to prior art FIGS. 1 and 2, the left gastric artery (LGA) 10 branches off the aorta 12 and encircles the stomach 14. The first branch from the left gastric artery 10 supplies the esophagus (E) 22, which then extends into vessels which supply the fundus (F) 16 and subsequently into body (B) 18 and the lower antrum 20. Eventually, the left gastric artery (LGA) 10 connects to the right gastric artery (RGA), which provides a duplicate blood supply to the stomach. It is important to note that both the RGA and LGA can provide flow to the fundus.

The target zone for embolic infusion is the fundus 16, which is more resilient to ischemia from embolization and provides the therapeutic effect of weight loss through multiple mechanisms including reduced ghrelin, reduced gastric motility, reduced acid production, and other functional and hormonal changes.

In the current method of gastric artery embolization, a modified Seldinger technique is utilized to perform an intra-arterial infusion in the stomach. Entry is made at the femoral artery, and the infusion device is advanced via a delivery system up the aorta to the celiac axis. The infusion device is then selectively advanced into the left gastric artery, advanced past the esophageal artery, and advanced into several of the many vessels feeding the fundus. The left gastric artery proceeds distal to the fundus and supplies blood to tissue in the body of the stomach. The embolic agent is infused into the infusion device at various locations in one or many vessels supplying the fundus. The infusion device may be re-positioned during the procedure to reach target tissue.

Embolic agent that flows proximal to or beyond the fundus will embed in non-target tissues. This is particularly so if the physician infuses within the presence of slow flow or stasis. In such case, reflux of embolic agent may occur into the esophageal branch of the LGA. Further, if the physician infuses with too great pressure, the embolic agent can be infused to non-target vessels of the body or the antrum of the stomach or even outside the stomach. This is particularly problematic, as the arteries of the stomach, the esophageal arteries 22 and the hepatic arteries (not shown) are continuous with each other, and feed from one to the other.

Therefore, while embolizing agent therapies which are considered minimally or limited invasive often provide good results, the potential for non-targeted embolization which can lead to adverse events and morbidity exists. Current methods do not control flow or pressure and leave both distal and proximal vessels that lead to non-target areas in the stomach patent during infusion and therefore in danger of inadvertent infusion.

Often, interventional radiologists try to reduce the amount and impact of reflux by slowly releasing the embolizing agent, by delivering a reduced dosage, or by super-selecting out multiple tiny branches of the target tissue. The added time, complexity, increased radiation dose to the patient and physician (longer monitoring of the patient) and potential for reduced efficacy make the slow delivery of embolization agents suboptimal. Reducing the dosage often leads to the need for multiple follow-up treatments. Finally, requiring super selective infusion in multiple small fundal vessels significantly increases procedure time and the potential for arterial vasospasm and dissection, limiting efficacy and potentially hurting the patient. Even when the physician tries to reduce the amount of reflux, the local flow conditions at the tip of the microcatheter change too fast to be controlled by the physician, and therefore rapid momentary reflux conditions can happen throughout infusion.

It is essential that the bariatric embolization procedures have a high safety profile in order to be widely adopted as a superior minimally invasive bariatric procedure.

SUMMARY OF THE INVENTION

A method of gastric arterial embolization is provided. The method includes deploying a pressure modulating device in a manner that infuses the embolizing agent into the fundus, but reduces or prevents delivery of the agent into proximal and distal non-target vessel. Such non-target vessels include the body and antrum of the stomach as well as the esophagus and liver with which the left gastric artery communicates. The fundus is the target for the bariatric embolization and has the highest blood flow and pressure drop from the left gastric artery. The method takes advantage of unique flow and pressure dynamics of the arterial vessels in the stomach.

In accord with the method, a modified Seldinger technique is utilized to introduce a delivery system for an infusion device up the aorta to the celiac axis. A pressure reducing infusion device (PRID) is then advanced into the left gastric artery, and deployed at a target location distal of esophageal artery and proximal to the arteries leading directly to the fundus. The pressure reducing infusion device is preferably a microvalve filter device, but alternatively can be an inflatable balloon catheter or other suitable device. Then, in a pressure targeting mode, a contrast agent is infused through the pressure reducing infusion device and the stomach is examined using a visualization technique such as fluoroscopy. If the contrast agent has been delivered to proximal or distal non-target vessels, then the pressure reducing infusion device is slightly expanded at the target location to increase its diameter within the vessel and generate a pressure drop in the arterial vessel of the stomach between the proximal and distal sides of the pressure reducing infusion device. It is important to note the stomach is supplied by both the left gastric artery (LGA) and the right gastric artery (RGA). The more the PRID is expanded, the greater flow is provided by the RGA, which provides blood supply that does not have embolic agents. Pressure targeting is repeated until only the larger flow arteries targeting the fundus are confirmed receiving contrast agent under visualization. Once targeting of the intended arteries is confirmed, embolic agent is infused (preferably together with additional contrast agent). Infusion is stopped once a dose of the embolizing agent has been delivered. After delivery of the embolizing agent, the pressure reducing infusion device and delivery system are withdrawn, and an arterial closure device is used to close the entry wound in the femoral artery.

BRIEF DESCRIPTION OF DRAWINGS

Prior art

Prior art

DETAILED DESCRIPTION OF THE PREFERRED EMBODIMENTS

Figure 1A:
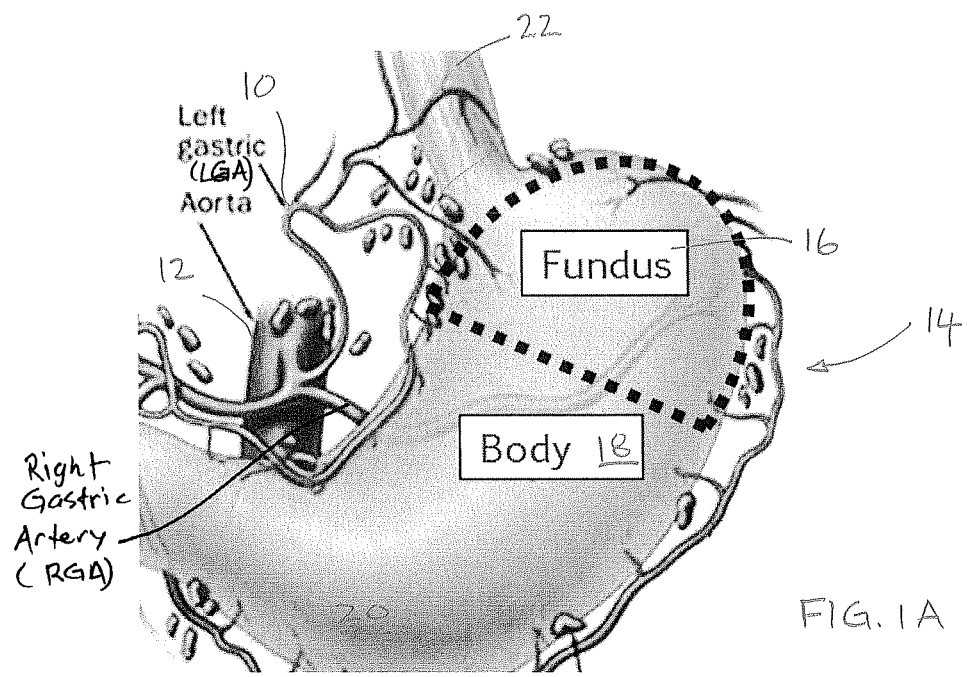
FIG. 1A illustrates the stomach and selected surrounding structure.
Figure 1B:
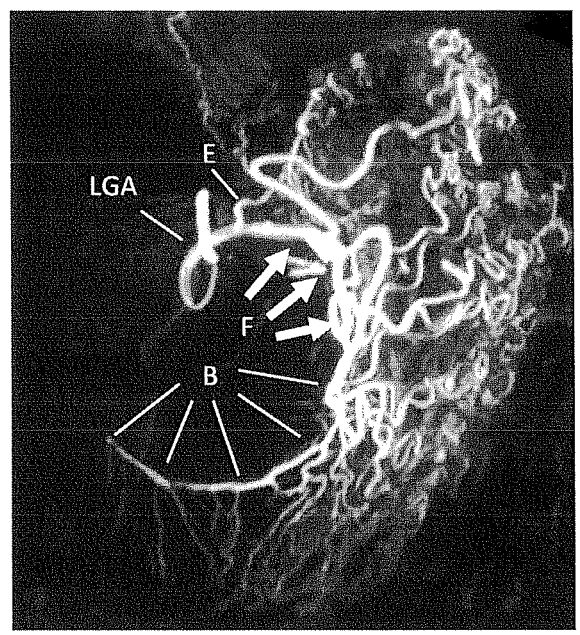
FIG. 1B is a fluoroscopic image of the left gastric artery accessed from the celiac trunk.

With reference to the human body and components of the devices and systems described herein which are intended to be hand-operated by a user, the terms "proximal" and "distal" are defined in reference to the user's hand, with the term "proximal" being closer to the user's hand, and the term "distal" being further from the user's hand, unless alternate definitions are specifically provided.

Methods are provided herein for gastric arterial embolization suitable for bariatric treatment. A preferred methodology has been determined for infusing the left gastric artery and its large branch vessels within the fundus with an embolizing agent while maintaining other tissues within the stomach as well as other organs having vessels in direct and indirect communication with the left gastric artery free (or at least substantially free) of the embolizing agent. As can be appreciated, this provides preferred results over current practices in terms of a desirable safety profile and faciliates delivery of the prescribed dose of embolizing agent to solely the intended target tissue.

In accord with the procedure, a modified Seldinger technique is utilized to introduce a delivery system for an infusion device up the aorta to the celiac axis. The delivery system may comprise a delivery catheter. In the Seldinger technique, which is well-known and will not be described in detail herein, access is provided from the thigh to the femoral artery and a guidewire is advanced to the aorta. The delivery catheter is advanced over the guidewire. Once the delivery catheter is at its intended position, and in accord with the method herein, a pressure reducing infusion device (PRID) is advanced through the delivery catheter and over the guidewire. The invention is not limited to such delivery methods, and any other method or system to intravascularly advance a PRID to the target location, described below, is also contemplated to be within the scope of the invention.

The PRID generally includes two requisite features. First, the PRID includes an infusion lumen and distal orifice through which an embolizing agent can be infused into the arterial vessel. Second, and in distinction from a simple microcatheter, the PRID includes expandable structure that can be expanded within the vessel, selectively between a non-expanded state, various partially expanded states within the vessel, and a fully expanded stated within the vessel so as to be in contact with the vessel wall. In the preferred devices, the expandable structure is located entirely proximal to the lumen orifice; however, it may alternatively be flush with the distal end of the expandable structure or even recessed relative to the expandable structure. During each of the various partial states and fully expanded states within the arterial vessel, the PRID modifies the distal pressure within the vessel relative to the non-expanded state. The significance of the PRID and its operation to facilitate and enhance embolic infusion specifically within the fundus is discussed below.

Figure 2A:
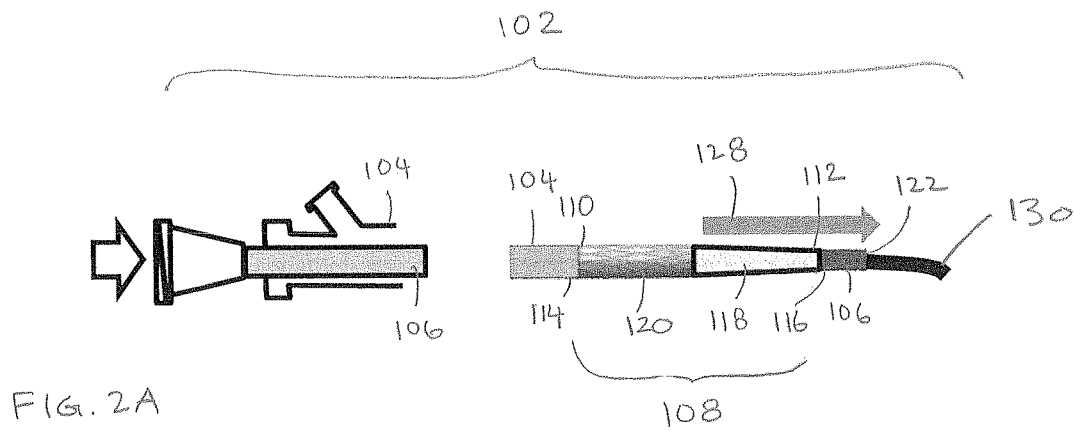
FIGS. 2A-2C are schematic illustrations of a first exemplar embodiment of a pressure reducing infusion device (PRID) in collapsed, partially expanded, and fully expanded configurations, respectively.
Figure 2B:
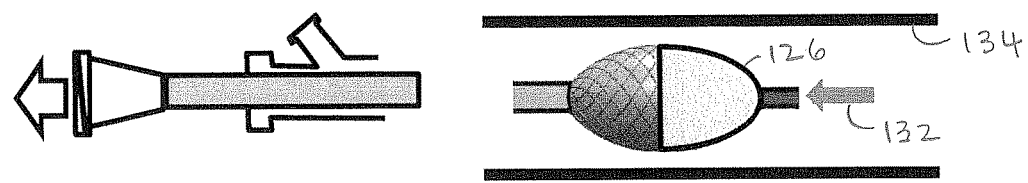
Figure 2C:
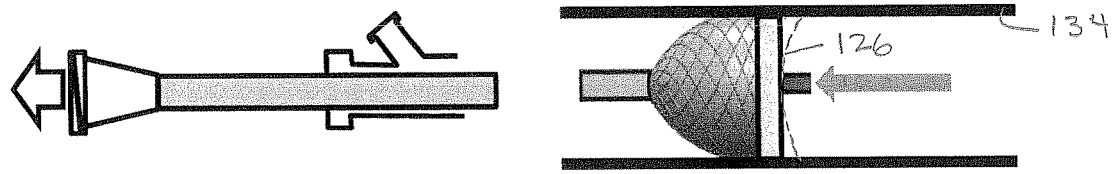

Referring to FIGS. 2A-2C, in one embodiment of a PRID, the expandable structure is a microvalve device 102 that is operable between non-expandable and expandable configurations by manual control at a proximal end of the instrument. Such a microvalve device is described in detail in previously incorporated U.S. Ser. No. 14/259,293. Generally, a PRID instrument with microvalve device 102 more particularly includes an outer catheter 104, an inner infusion catheter 106 extending through the outer catheter, and a dynamically adjustable microvalve 108 coupled to both of the outer and inner catheters 104, 106. The microvalve 108 includes a portion constructed with a naturally spring-biased filamentary braid construction that is biased to radially expand. The microvalve 108 has a proximal end 110 and a distal end 112. The proximal end 110 of the microvalve is coupled to a distal end 114 of the outer catheter 104, and the distal end 112 of the microvalve is coupled to a distal end 116 of the inner catheter 106. The microvalve 108 has a closed filtering distal portion 118, preferably made from a porous polymeric material defining a pore size not exceeding 500 μm, and a proximal and distal portions 120, the portions joined at their respective circumferences at the maximum diameter portion of the microvalve. The inner infusion catheter 106 is configured to deliver a therapeutic embolic agent through an orifice 122 that opens distal of the closed distal portion 118 of the microvalve.

The microvalve 108 can be manually displaced between open and closed configurations by longitudinally displacing the distal end 116 of the inner catheter 106 relative to the distal end 114 of the outer catheter 104 by moving the proximal end of one of the catheters relative to the other. By displacing the inner catheter 106 distally (in the direction of arrow 128) relative to the outer catheter 104, the microvalve 108 is moved into a collapsed configuration, suitable for delivery to the treatment site, as shown in FIG. 2A. In this collapsed configuration, the distal portion 118 is formed into a tip that is tapered to assume a form that has excellent trackability over a guidewire 130 to be advanced to the treatment site.

To deploy and expand the microvalve 108, the inner catheter 106 can be refracted (in the direction of arrow 132) a selected distance relative to the outer catheter 104 to cause the microvalve 108 to reconfigure, resulting in radial expansion toward (FIG. 2B) or even all the way to a vessel wall 134 (FIG. 2C). The degree of expansion is accurately controllable via relative movement at the proximal end of the instrument 102. Such movement can be finely controlled with an appropriate handle, including, by way of example only, a slider or rotation knob (not shown) coupled to the respective proximal ends of the inner and outer catheters 104, 106. When the microvalve 108 is partially expanded, the partially refracted shape of the microvalve 108 presents a distal face 126 with a shape that is convex toward the upstream flow (FIG. 2B). When the microvalve is expanded completely to the vessel wall, the microvalve preferably has a distal face 126 that is planar or concave as presented to upstream flow (FIG. 2C). In addition, the spring-bias of the microvalve 108 also operates to assist in radially expanding the microvalve, particularly when subject to a pressure differential on opposing sides of the microvalve.

The proximal portion 120 of the microvalve preferably has a different radial expansion force than the distal portion 118 of the microvalve. More preferably, the proximal portion 120 has a substantially greater radial expansion force than the distal portion. With the microvalve 108 in a deployed open configuration, i.e., with the distal tip in a retracted position relative to the delivery position, the microvalve remains dynamically responsive to local pressure about the microvalve. Given the structural dynamic property of the microvalve, even if the microvalve is expanded fully to the vessel wall, under the dynamically responsive operation, substantially unrestricted downstream (forward) flow of blood in the vessel is permitted, while (upstream) reflux or backflow is prevented to stop reflux of the therapeutic agent within the vessel. Similarly, if the microvalve is only partially expanded within the vessel, the microvalve is dynamically responsive to pressure conditions of the flow in the vessel.

Figure 3A:
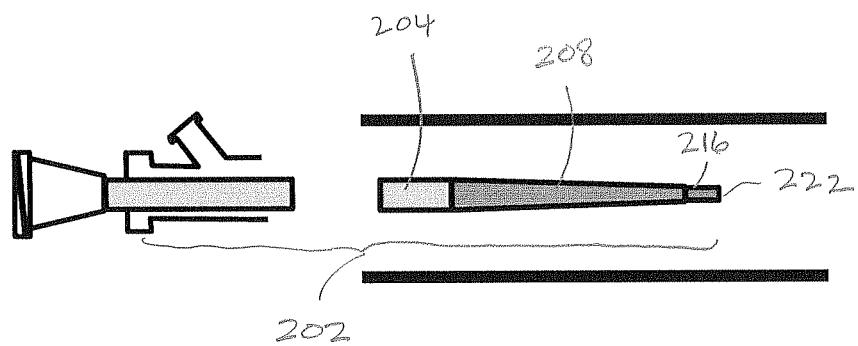
FIGS. 3A-3C are schematic illustrations of a second exemplar embodiment of a pressure reducing infusion device (PRID) in collapsed, partially expanded, and fully expanded configurations, respectively.
Figure 3B:
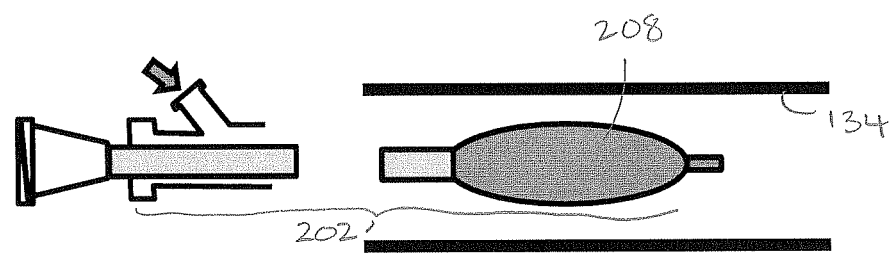
Figure 3C:
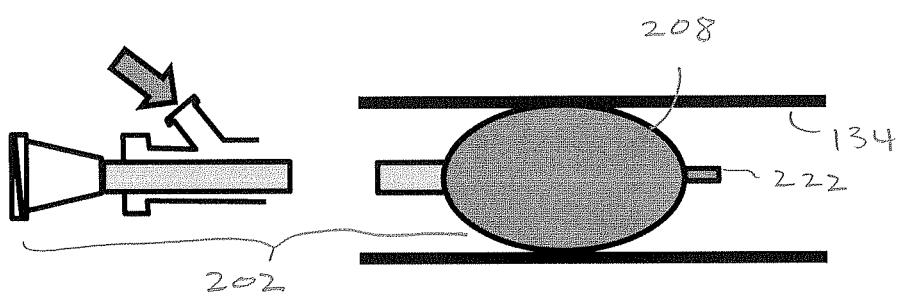

Turning now to FIGS. 3A-3C, the PRID may also be a balloon catheter device. By way of example, the balloon catheter device 202 includes a catheter 204 having a first lumen for infusing the embolizing agent out of a distal orifice 222, and a second inflation lumen (not shown). An elastic membrane is provided about the distal portion 216 of the catheter and has a lower surface in communication with the inflation lumen to define a fluid inflatable balloon 208. FIG. 3A shows the balloon 208 in a collapsed configuration, FIG. 3B shows the balloon 208 in a partially expanded configuration (i.e., expanded insufficiently to reach across the vessel walls 134), and FIG. 3C shows the balloon 208 in a fully expanded configuration (i.e., expanded fully to the vessel walls 134). It is preferred that the balloon 208 be proximally offset from the tip of the catheter and particularly the orifice 222 of the first lumen. The balloon catheter device 202 may additionally include multiple balloons, optionally of different sizes, and either radially or longitudinally offset.

Figure 4A:
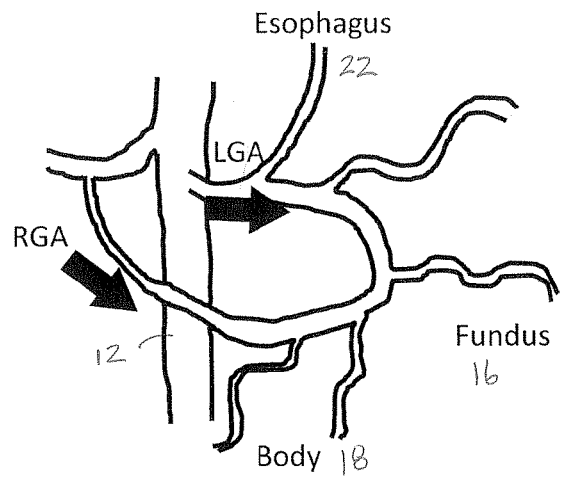
FIG. 4A-4D are schematic illustrations of a method of the invention, including illustrating that the RGA and LGA supply the stomach from two different sides (FIG. 4A) advancing the PRID to a target location (FIG. 4B), using the PRID in a targeting mode to determine and establish an appropriate vascular pressure in which to infuse an embolizing agent (FIG. 4C), and using the PRID to infuse an embolizing agent into the large vessels of the fundus and in a manner that prevents flow to the body of the stomach (FIG. 4D).
Figure 4B:
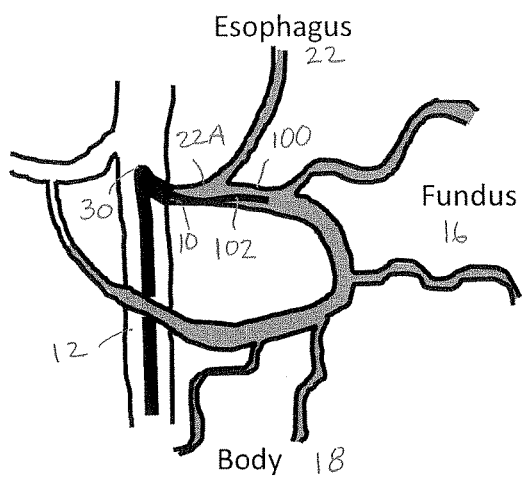
Figure 4C:
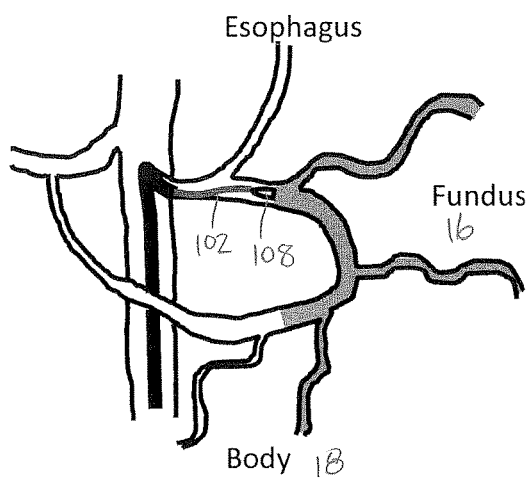
Figure 4D:
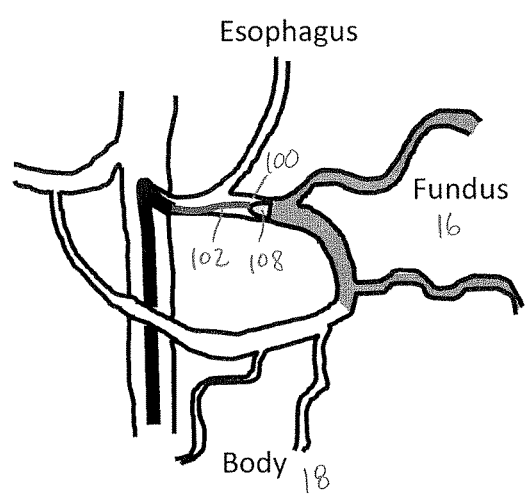

The PRID, in any suitable form (device 102 referred to hereinafter by way of example only), is advanced up the aorta 12 to the celiac axis 30, and eventually into the left gastric artery 10 (FIG. 4A). From the left gastric artery 10, the PRID 102 is further advanced past the esophageal artery 22A and then advanced to a target location 100 proximal to several of the many vessels feeding the fundus 16 (FIG. 4B). The PRID 12 is then infused with a contrast agent under fluoroscopy in a pressure targeting mode as follows. The PRID 102 is first configured in a relatively collapsed configuration. The relatively collapsed configuration includes a fully collapsed configuration, such as shown in FIGS. 2A and 3A, or a substantially collapsed configuration; i.e., substantially more collapsed than open. Then, a contrast agent 200 adapted to fluoresce under radiographic visualization is infused through the infusion lumen of the PRID 102 and out of its distal orifice 122 while the stomach is examined under fluoroscopy. With the microvalve 108 of the PRID 102 (or balloon 208 of PRID 202) in a relatively collapsed configuration, the vascular travel of the contrast agent 200 is observed under fluoroscopy. If the contrast agent is delivered to non-target vessels, either proximally (in reflux) or distally beyond the fundus 16 to the body 18 (both as shown in FIG. 4B), then the microvalve 108 of the PRID 102 is reconfigured at the target location into an expanded slightly larger diameter for subsequent observation in targeting mode. Significantly, given the target location of the PRID, this expanded reconfiguration results in a pressure drop in the fundus 16 and alters the path of the contrast agent 200 as well as subsequently infused embolizing agent in a subsequent step of the method. The contrast agent 200 is again infused through the infusion lumen of the re-sized microvalve 108 of the PRID 102 and out of the orifice and the vascular travel of the contrast agent is again observed. FIG. 4B illustrates that the altered pressure in the vessels created by the expanded microvalve 108 of the PRID 102 prevents refluxing of the contrast agent (even when the microvalve is not expanded to the vessel walls), but continues to allow contrast agent downstream to the larger non-target vessels of the body 18 of the stomach. Re-sizing of the microvalve 108 of the PRID 102 and the consequent downstream pressure drop is repeated until only the larger flow arteries of the fundus 16 are targeted, as confirmed with contrast agent visualization under fluoroscopy, and the arteries serving the body 18 of the stomach receive blood flow from the RGA instead of the LGA, which is observable when the fundal vessels are not receiving any (or any appreciable amount) of contrast agent, as seen in FIG. 4C. It is, of course, possible that targeting mode will confirm proper configuration of the PRID upon initial infusion of the contrast agent, and that the PRID will not be required to be altered in expansion to reduce downstream pressure to target only the larger flow arteries. Alternatively, one can work in reverse; i.e., starting with the PRID fully expanded and decreasing its size until only the larger flow arteries feeding feeding the fundus are enhanced under fluroscopy. Depending on the dosage intended for the patient, the treatment may be considered complete if sub-stasis (slow flow) is observed, or stasis (no flow) is observed (i.e., without reflux in the case of the anti-reflux system). With the PRID, the treatment may also be performed beyond stasis by either fully inflating the balloon or using an anti-reflux infusion system to infuse a greater embolic load than would be achievable with a traditional catheter (since all or most of the embolic agent would reflux in stasis conditions). This method provides significantly greater control over dosing than a traditional microcatheter method.

Once targeting of only the intended larger flow arteries of the fundus 16 is confirmed, embolic agent is infused through the infusion lumen of the sized PRID 102 (preferably together with additional contrast agent under visualization of fluoroscopy). Infusion continues, preferably until the intended dose of embolizing agent has been completely delivered.

Figure 5:
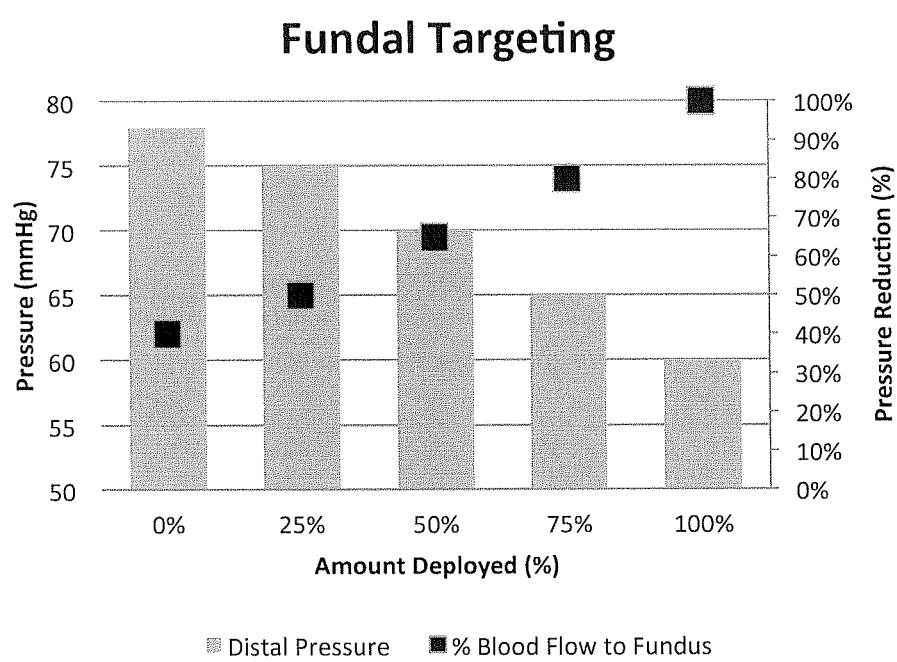
FIG. 5 is a graph of fundal flow targeting with the PRID relative to the expansion of the PRID.

Referring to FIG. 5, given the unique flow characteristics of the vessels of the stomach, it is appreciated that as the PRID is expanded within the vessel at the target location; i.e., distal of the esophageal artery and proximal of the fundus arteries, (i) the downstream pressure at the target location drops, (ii) the blood flow to the fundus increases, (iii) the upstream and downstream pressure at non-target locations is not subject a decrease, and (iv) blood flow to non-target locations does not increase. These parameters allow the embolization agent to be particularly targeted to the intended location so that the prescribed dose is delivered to the fundus and also so that agent is not delivered to unintended tissue both proximally and distally of the fundus.

After delivery of the embolic agent, the infusion device and delivery system are collapsed and withdrawn, and an arterial closure device is used to close the entry wound in the femoral artery.

There have been described and illustrated herein methods of bariatric embolization. While particular embodiments of the invention have been described, it is not intended that the invention be limited thereto, as it is intended that the invention be as broad in scope as the art will allow and that the specification be read likewise. Thus, while particular pressure reducing infusion devices (PRID) have been described, it is anticipated that other PRIDs may be used in the methods described herein. That said, it is anticipated that the manually adjustable, but dynamically adjustable microvalve which has superior operating characteristics in a vessel will be optimum for the procedure for its ability to provide fine pressure control relative to the expandable microvalve while continuing to permit downstream blood flow. Also, while the method described herein has been primarily directed to bariatric embolization, it is appreciated that it can be similarly used to direct infusion of other therapeutic treatments to the fundus over other tissues of the stomach and connected tissues. Further, while embolization of the fundus has been described with respect to providing a bariatric treatment, it is recognized that there are potential other therapeutic benefits of infusing an embolizing agent to the fundus, and such resulting treatments are within the scope of the invention. It will therefore be appreciated by those skilled in the art that yet other modifications could be made to the provided invention without deviating from its scope as claimed.

What is claimed is:

1. A method of delivering a therapeutic agent to a fundus of a stomach, comprising:
   a) advancing a pressure reducing infusion device (PRID) to a target location distal of an esophageal artery and proximal to an artery leading to a fundus of a stomach;
   b) after the PRID is at the target location, infusing a contrast agent through the PRID;
   c) monitoring the contrast agent under a visualization technique;
   d) from the monitoring, determining an extent of delivery of the contrast agent to vessels outside the fundus;
   e) reducing the intravascular pressure distal of the PRID;
   f) repeating steps b)-e) until contrast agent is delivered to vessels substantially only within the fundus; and
   g) infusing therapeutic agent at the target location to treat the fundus.

2. A method according to claim 1, wherein the therapeutic agent is infused together with additional contrast agent.

3. A method according to claim 1, wherein the therapeutic agent is an embolization agent.

4. A method according to claim 1, wherein the PRID is a microvalve filter device.

5. A method according to claim 4, wherein the PRID includes,
   i) a flexible outer catheter having a proximal end and a distal end,
   ii) a flexible inner catheter having a proximal end and a distal end with an orifice, the inner catheter extending through and longitudinally displaceable relative to the outer catheter, and
   iii) a microvalve having a proximal end and distal end, the proximal end of the microvalve coupled to the distal end of the outer catheter, and the distal end of the microvalve coupled to the inner catheter adjacent the distal end of the inner catheter, such that longitudinal displacement of the inner catheter relative to the outer catheter moves the microvalve from a non-deployed configuration to a deployed configuration, the microvalve having a proximal portion and distal portion, and a maximum diameter of the microvalve being defined between the proximal and distal portions, the proximal portion exerting an increased radial force relative to the distal portion.

6. A method according to claim 5, wherein the distal portion of the PRID comprises a porous polymeric material defining a pore size not exceeding 500 μm.

7. A method according to claim 1, wherein the PRID is an inflatable balloon catheter device.

8. A method of performing bariatric embolization, comprising:
   a) advancing a pressure reducing infusion device (PRID) to a target location distal of an esophageal artery and proximal to an artery leading to a fundus of a stomach;
   b) after the PRID is at the target location, infusing a contrast agent through the PRID;

c) monitoring the contrast agent under a visualization technique;

d) from the monitoring, determining an extent of delivery of the contrast agent to vessels outside the fundus;

e) expanding the PRID at the target location to cause a pressure drop distally of the PRID;

f) repeating steps b)-e) until contrast agent is delivered to vessels substantially only within the fundus; and g) once it is determined that the contrast agent is delivered to vessels substantially only within the fundus, infusing embolization agent at the target location to embolize the vessels substantially only within the fundus.

9. A method according to claim 8, wherein the embolization agent is infused together with additional contrast agent.

10. A method according to claim 8, wherein the PRID is a microvalve filter device.

11. A method according to claim 10, wherein the PRID includes, i) a flexible outer catheter having a proximal end and a distal end, ii) a flexible inner catheter having a proximal end and a distal end with an orifice, the inner catheter extending through and longitudinally displaceable relative to the outer catheter, and iii) a microvalve having a proximal end and distal end, the proximal end of the microvalve coupled to the distal end of the outer catheter, and the distal end of the microvalve coupled to the inner catheter adjacent the distal end of the inner catheter, such that longitudinal displacement of the inner catheter relative to the outer catheter moves the microvalve from a non-deployed configuration to a deployed configuration, the microvalve having a proximal portion and distal portion, and a maximum diameter of the microvalve being defined between the proximal and distal portions, the proximal portion exerting an increased radial force relative to the distal portion.

12. A method according to claim 11, wherein the distal portion of the PRID comprises a porous polymeric material defining a pore size not exceeding 500 μm.

13. A method according to claim 8, wherein the PRID is an inflatable balloon catheter device.

* * * * *